United States Patent
Petros

(10) Patent No.: US 8,753,372 B2
(45) Date of Patent: Jun. 17, 2014

(54) ANCHORING DEVICE AND ITS IMPLEMENTATION

(75) Inventor: Peter Emmanuel Petros, Claremont (AU)

(73) Assignee: Kvinno Centre Pty Ltd, Claremont, Western Australia (AU)

(*) Notice: Subject to any disclaimer, the term of this patent is extended or adjusted under 35 U.S.C. 154(b) by 1086 days.

(21) Appl. No.: 10/524,701

(22) PCT Filed: Aug. 15, 2003

(86) PCT No.: PCT/AU03/01036
§ 371 (c)(1),
(2), (4) Date: Feb. 16, 2005

(87) PCT Pub. No.: WO2004/017845
PCT Pub. Date: Mar. 4, 2004

(65) Prior Publication Data
US 2005/0256530 A1    Nov. 17, 2005

(30) Foreign Application Priority Data

| Aug. 13, 2002 | (AU) | 2002951024 |
| Oct. 17, 2002 | (AU) | 2002952128 |
| May 23, 2003 | (AU) | 2003902559 |

(51) Int. Cl.
*A61B 17/04* (2006.01)
(52) U.S. Cl.
USPC ........................ 606/232; 606/151
(58) Field of Classification Search
USPC ........ 606/151, 232–233, 224, 75, 139–148; 24/115 R, 132 R, 132 AA
See application file for complete search history.

(56) References Cited

U.S. PATENT DOCUMENTS

| 1,605,503 | A | * | 11/1926 | Boenning | 24/132 R |
| 5,242,457 | A | * | 9/1993 | Akopov et al. | 606/144 |
| 5,370,662 | A | | 12/1994 | Stone et al. | |
| 5,417,712 | A | * | 5/1995 | Whittaker et al. | 606/232 |
| 5,423,860 | A | * | 6/1995 | Lizardi et al. | 606/232 |
| 5,662,654 | A | * | 9/1997 | Thompson | 606/232 |
| 5,669,935 | A | * | 9/1997 | Rosenman et al. | 606/232 |
| 5,702,397 | A | * | 12/1997 | Goble et al. | 606/232 |

(Continued)

FOREIGN PATENT DOCUMENTS

| EP | 0558993 | 9/1993 |
| EP | 0713683 | 5/1996 |

(Continued)

OTHER PUBLICATIONS

Gyneideas; Product Portfolio; www.gyneideas.com/portfolio.htm; Oct. 31, 2003.

*Primary Examiner* — Mark Mashack
(74) *Attorney, Agent, or Firm* — Gottlieb, Rackman & Reisman, P.C.

(57) ABSTRACT

Anchor (115) particularly useful for providing ligamentory support between two spaced locations in the body of a patient includes a base (153), a head (157) having a configuration to facilitate insertion of the head into the tissue and retention of the head in the tissue once inserted. The base is formed with an aperture (161) adapted to receive a length of a filamentary element (127) and permit slidable movement of the filamentary element through the aperture in one direction. Movement of the filamentary element in the opposite direction through the aperture is prevented by a locking element.

22 Claims, 20 Drawing Sheets

(56) References Cited

U.S. PATENT DOCUMENTS

| | | | |
|---|---|---|---|
| 5,741,301 A * | 4/1998 | Pagedas | 606/232 |
| 5,891,168 A * | 4/1999 | Thal | 606/232 |
| 5,944,739 A | 8/1999 | Zlock et al. | |
| 6,015,428 A * | 1/2000 | Pagedas | 606/232 |
| 6,066,160 A * | 5/2000 | Colvin et al. | 606/232 |
| 6,139,565 A | 10/2000 | Stone et al. | |
| 6,174,323 B1 * | 1/2001 | Biggs et al. | 606/232 |
| 6,334,446 B1 | 1/2002 | Beyar | |
| 6,599,311 B1 * | 7/2003 | Biggs et al. | 606/232 |
| 2002/0065528 A1 | 5/2002 | Clark et al. | |
| 2003/0088250 A1 * | 5/2003 | Colleran et al. | 606/72 |
| 2003/0120309 A1 | 6/2003 | Colleran et al. | |
| 2003/0130669 A1 * | 7/2003 | Damarati | 606/151 |

FOREIGN PATENT DOCUMENTS

| | | |
|---|---|---|
| FR | 2731610 | 9/1996 |
| JP | 08-196546 | 8/1996 |
| WO | WO 99/59477 | 11/1999 |
| WO | 01/67962 | 9/2001 |
| WO | WO 01/67962 A2 | 9/2001 |
| WO | 02/30293 | 4/2002 |
| WO | WO 02/30293 A1 | 4/2002 |

* cited by examiner

ANCHORING DEVICE AND ITS IMPLEMENTATION

This invention, which claims the priority date of Australian Patent Application 2002951024 filed Aug. 13, 2002; Australian Patent Application 2002952128 filed Oct. 17, 2002; and; Australian Patent Application 2003902559 filed May 23, 2003; relates to an anchor which can be used in surgical procedures on both humans and animals.

This invention relates to an anchor which can be used in surgical procedures on both humans and animals.

BACKGROUND ART

The invention has application to a wide variety of surgical procedures and one such procedure relates to a method of resolving female incontinence, which involves insertion of a filament which is to be fixed to the ligamentous tissue to either side of the vagina in order to reconstitute the ligamentary support for the urethra and/or vaginal wall. In the past such filaments have either been fixed to the pubic bone or alternatively the rectus abdominous muscle or left "tension free" in that muscle.

The inventor is the principal author of an article entitled "Role of the Pelvic Floor in Bladder Neck Opening and Closure II: Vagina" which appeared in the International Urogynecology Journal (1997) 8:69-73. In that article it was identified the "connective tissue laxity in the vagina or its supporting ligaments is the prime cause of symptoms of stress, urgency and abnormal emptying". As a result in the case of a lax vagina, at least some of the muscular activity which is applied to maintain continence is taken up in resolving the vaginal laxity rather than control of the urethra. Therefore in rectifying the problem it is desirable to establish a situation in which the relationship between the existing muscular and ligamentory support can be reestablished

DISCLOSURE OF THE INVENTION

Accordingly in one aspect the invention resides in a method of providing ligamentory like support between two spaced locations in the body of a patient wherein the locations comprise ligament and/or muscle tissue comprising fixing an anchor in each location, connecting the anchors by a filamentary element, adjusting the tension of the filamentary element between the locations to establish the desired spatial relationship between the locations to provide at least a supplementary ligamentory support between the locations.

According to a preferred feature of the invention the locations comprise ligament and/or muscle tissue.

According to a preferred feature of the invention the anchors are provided with a retaining means adapted to be able to retain the filamentary element in optimal tension between the anchors.

According to a preferred feature of the invention the retaining means enables movement of the filamentary element through the anchor to enable the length of the filamentary element between the locations to be shortened but to prevent movement of the filamentary element through the anchors to enable the length of the filamentary element between the applications to be increased.

According to a further preferred feature of the invention the filamentary element is not biodegradable over a period of time and is adapted to facilitate the growth of tissue between the locations to provide said ligamentory support between the locations.

According to a preferred feature of the invention the anchor comprises a head having a configuration facilitating insertion into the tissue and retention of the head in the tissue once inserted, the anchor further having a base which is intended to receive the filamentary element, said method comprising inserting the head of the anchor into the tissue with the base buried in the tissue.

According to a further preferred feature of the invention the head has a barbed configuration. According to a preferred feature of the invention the barbed configuration comprises a set of prongs extending in a divergent manner from the end of the head towards the base, said prongs being resiliently flexible along their length, said method comprising compressing the ends of the prongs towards each other prior to insertion of the head into the tissue, inserting the head into the tissue and releasing the ends of the prongs once the head is located in the tissue.

According to a further preferred feature of the invention the anchor is associated with a holder which is configured to retain the anchor with the head directed outwardly from the holder, the method comprising installing an anchor in the holder and placing the anchor in position in the tissue by means of the holder, subsequently disengaging the holder from the anchor. According to a preferred feature of the invention the filamentary element is installed in the anchor and the anchor is installed on the holder prior to insertion of the head into the tissue. According to a preferred feature of the invention the holder is adapted to receive and support the prongs in their compressed state, said method comprising releasing the prongs from engagement with the holder when the anchor is in position.

According to a further preferred feature of the invention the holder is associated with an insertion appliance, the insertion appliance having a shaft, one end of the shaft adapted to receive the holder, the other end of the shaft supporting the handle, an ejection means extending between the handle and the one end and having a bearing member at one end adapted to bear upon an anchor when installed in the holder, the handle provided with a manipulation member adapted to cause the bearing member to bear on the anchor and cause the displacement of the anchor from the holder, said method comprising locating the holder at the one end of the shaft, installing an anchor into the holder, placing the anchor in position in the tissue by manipulation of the appliance and on location of the anchor in the tissue, activation of the manipulation means to cause displacement of the anchor from the holder.

According to a preferred feature of the invention the spaced locations comprise the recto-vaginal ligaments or the arcus tendineus ligaments to each side of the vagina and the method resides in the re-establishing of the fascial support for the vagina, said method comprising fixing said anchors into the recto-vaginal ligaments or the arcus tendineus ligaments respectively to each side of the vagina, applying the filamentary element between the anchors and introducing the filamentary element into the fascial tissue such that with time it will become embodied with the fascia and optimally tensioning the filamentary element between the anchors.

According to a preferred feature of the invention the filamentary element is applied to at least one of the anchors prior to fixation. According to a preferred embodiment of the invention the filamentary element is applied to a pair of anchors at a spacing greater than that desired spatial relationship.

According to another aspect the invention resides in a tissue anchor formed of a material which is compatible for location in human and/or animal muscle and/or ligament tissue, the anchor comprising a base and a head, the head having a configuration to facilitate insertion of the head into tissue and retention of the head in the tissue once inserted, the base formed with an aperture adapted to receive a length of a filamentary element and permit slidable movement of the filamentary element through the aperture in one direction but to restrict movement of the filamentary element through the aperture in the opposite direction.

According to a preferred feature of the invention the aperture is associated with a locking element positioned to extend across the aperture to define a space between the locking element and an opposed edge of the aperture, said space being intended to receive the filamentary element, the locking member having one face proximate the one direction and another face proximate the opposite direction, the locking element intended to cooperate with the filamentary element when in position in the space to restrict the movement of the filamentary element in the opposite direction and to enable movement of the filamentary element in the one direction. According to a preferred feature the edge of the locking element defining the space is formed to engage the surface of the filamentary element when filamentary element is moved in the opposite direction. According to a preferred feature of the invention the edge is defined by a surface extending between the faces of the locking member, the surface being inclined away from the opposed edge of the aperture in the opposite direction. According to a preferred feature of the invention the edge is formed with slots which extend from the face proximate the one direction to at least an intermediate position across the surface. According to a preferred feature of the invention the face of the locking member proximate the one direction is formed as a recess inwardly of the edge. According to a preferred feature the locking member is inclined with respect to the base.

According to a preferred feature the space has a configuration substantially corresponding to the cross section of the filamentary element. According to a preferred feature of the invention the space has a configuration corresponding to the cross sectional configuration of the filamentary element when under longitudinal tension. According to a preferred feature of the invention the space has a part annular configuration. According to a preferred feature of the invention the opposed edge of the locking element which is remote from the head has a convex arcuate configuration. According to a preferred feature of the invention the space is located substantially centrally across the central longitudinal axis of the anchor.

According to a preferred feature of the invention the head has a barbed configuration. According to a preferred feature of the invention the barbed configuration of the head is defined by a set of prongs, said prongs being located in substantially equi-distant spacing around the central axis of the head, said prongs being divergent away from the end of the head in the direction of base.

According to a preferred feature of the invention the prongs are of a tapered configuration. According to a preferred feature of the invention the outer end of the prongs are pointed. According to a preferred feature of the invention the prongs are resiliently flexible along their length.

According to a further aspect the invention resides in a holder adapted to support the anchor as described above comprising a socket configured to clampingly receive the base, the socket being configured to allow access to the aperture, the clamping engagement between the holder and the base being such that on relative movement between the holder and the anchor the anchor is able to be disengaged from the holder.

According to a preferred feature of the invention the base has a substantially laminar-like configuration comprising two opposed substantially parallel faces.

According to a preferred feature of the invention the socket comprises a pair of spaced elements which receive opposed sides of the base with the aperture between the spaced elements.

According to a preferred feature of the invention the socket is defined by a set of boss elements which are configured to receive the free ends of the prongs of the anchor when compressed radially with respect to the central axis of the anchor.

According to a further aspect the invention resides in an insertion appliance comprising a shaft adapted to accommodate the holder as described above at one end, the other end of the shaft supporting a handle, an ejection means extending between the one end and the handle, a bearing member provided at the one end and a manipulation means provided adjacent the handle whereby on an anchor being installed in the holder and on activation of the manipulation means the bearing member will bear upon the anchor to move the anchor from engagement with the holder.

According to a preferred embodiment a holder of the form described above having an anchor of the form described above applied thereto are provided as a single element.

According to a preferred embodiment an insertion appliance of the form described above supporting a holder of the form described above having an anchor of the form described above applied thereto are provided as a single element.

The invention will be more fully understood in the light of the following description of several specific embodiments

BRIEF DESCRIPTION OF THE DRAWINGS

The description is made with reference to the accompanying drawings of which.

DETAILED DESCRIPTION OF SPECIFIC EMBODIMENTS

The method according to the first embodiment comprises utilisation of an anchor of the form described below as the second and third embodiments. The anchor provides a means of attaching a filament into muscle and/or ligamentary tissue. The anchor has a head which is able to be embedded into the tissue whereby once it is so embedded the anchor is retained in position. In addition the anchor has an attachment means which is able to receive and support a filament whereby the filament can slide through the attachment means in one direction but is restrained from slidable movement in the opposite direction.

It is the purpose of the procedure according to the embodiment to incorporate into the fascial tissue, which is located above and below the vaginal wall, a supporting filamentary element which is supported at either end from either the recto-vaginal ligaments or the arcus tendineus (A.T.F.P.) ligaments located to each side of the vagina.

Figure 1:
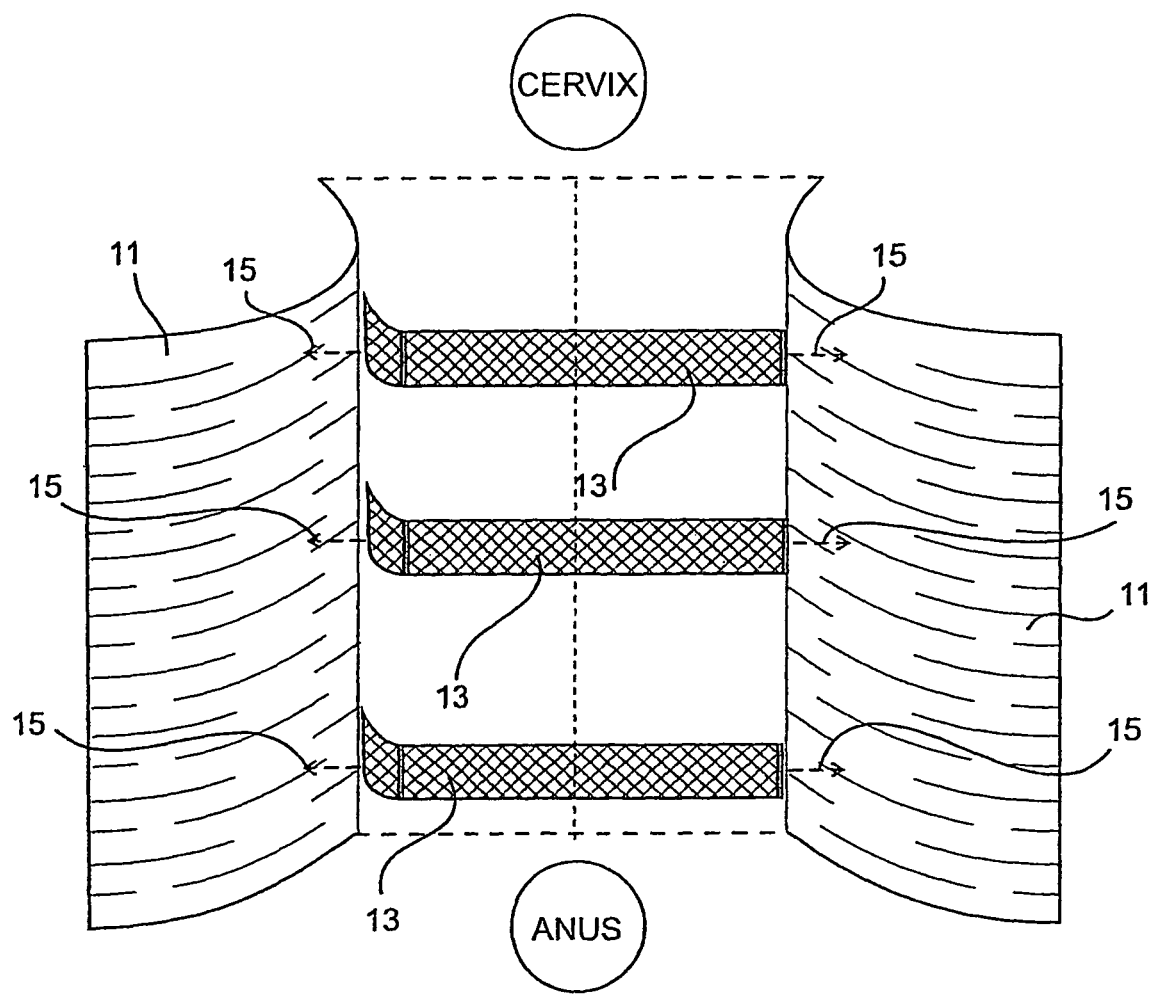
FIG. 1 is a schematic view of the posterior vaginal wall repair according to the first embodiment.
Figure 2:
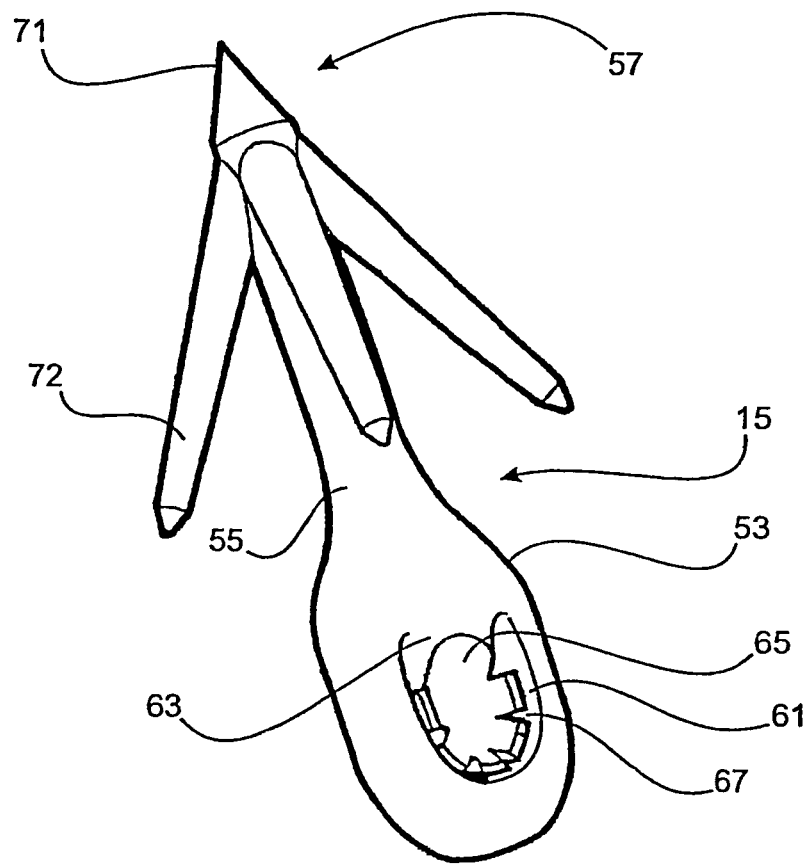
FIG. 2 is an isometric view of an anchor according to the second embodiment.
Figure 3:
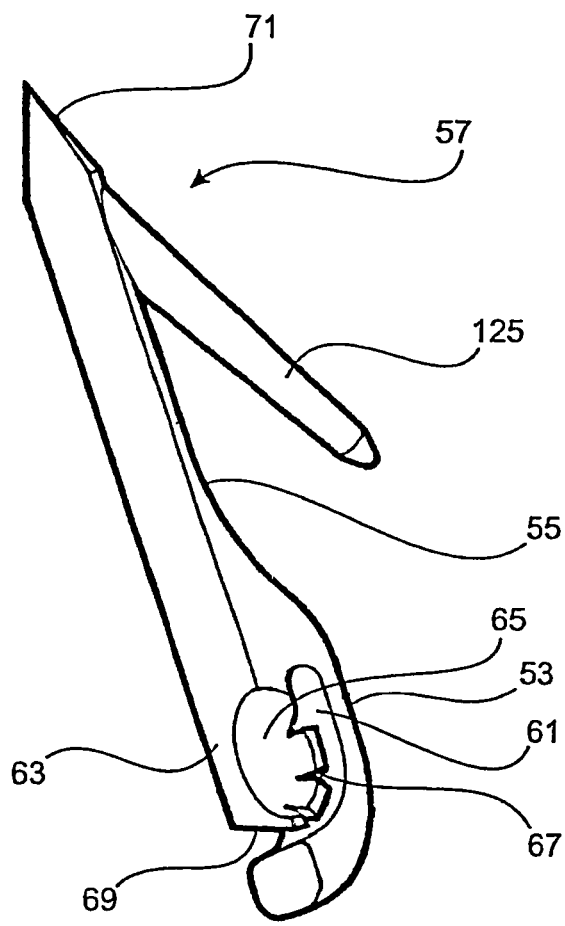
FIG. 3 is a sectional isometric view of the anchor of the second embodiment.

As shown in schematically at FIG. 1 the procedure according to the first embodiment involves forming a longitudinal incision in the anterior and/or posterior vaginal wall. This results in the creation of a pair of flaps 11 of fascial tissue to each side of the longitudinal incision. One or more lengths of filamentary element 13 are then fixed to each of either the recto-vaginal ligaments or the arcus tendineus (A.T.F.P.) ligaments which are located to each side of the vagina. The fixing of each length of filament is effected through a pair of anchors 15 of the form described below which receive the ends of the length of filament whereby because of the nature of the attachment means the spacing between the anchors 15 on the length of filamentary element 13 can be reduced by causing the filamentary element to be drawn through the attachment means of the anchor. The spacing between the anchors on the filamentary element cannot be increased. The anchors 15 on each length of filamentary element 13 are embedded into the recto-vaginal ligaments in opposed relationship to each side of the vagina. Once the anchors 15 are attached, the nature of the attachment means of the anchors enables the length of the filament 13 between the ligaments to be reduced and to introduce a degree of tension into the filamentary element between the ligaments. The flaps 11 of fascial tissue are then resutured into place. With the healing of the incisions the filamentary element becomes embodied into the fascial tissue on the anterior and posterior sides of the vaginal walls to provide reinforcement and support for that fascial tissue.

The tensioning of the filamentary element on its location in position between the recto-vaginal ligaments or the arcus tendineus (A.T.F.P.) ligaments enables the filamentary element to be precisely and sufficiently tightened to bring the fascia towards the mid-line and in so doing serves to repair any hernia. This serves to restore support for the vaginal wall and to facilitate the desired transmission of the muscle contraction to effect opening and closure of the urethra and anus without the muscle having initially to take up the laxity that previously existed in the connection between the fascial tissue and the recto-vaginal ligaments.

Each of the remaining embodiments are directed to an anchor which can be utilised in association with a filamentary element to enable the fixing and location of the filamentary element into a patient as described above in relation to the first embodiment.

The filamentary element which is used in the first embodiment and with which the second and third embodiments are used comprises a tape which is formed of a knitted or woven material where the material once located in the body will facilitate the growth of scar-like tissue upon it The anchor 15 according to the second embodiment is shown at FIGS. 2 to 5. The anchor is formed integrally of a suitable plastics material which may be biodegradable and comprises a base 53, a stem 55 which extends from the base 53 and a head 57 which is supported in spaced relation from the base 53 by the stem 55. The base is of a generally laminar configuration wherein the major faces of the base are substantially planar and parallel to the central axis of the stem 55. The base is formed with an aperture 61 which extends between the faces and which is associated with a locking member 63 which extends from the side of the aperture proximate the head 57 to terminate closely adjacent the other side of the aperture. The free end of the locking member has a convex arcuate configuration to cooperate with the other side of the aperture to define a part annular space. The spacing between the other side of the aperture and the free end of locking member approximately corresponds with the thickness of the filamentary element with which the anchor is to be used, when the filamentary element is tensioned.

The junction of the locking member with the one side of the aperture is such that the locking member can flex laterally out of the plane of aperture in one direction but is resistant to movement out of the plane aperture in the other direction. This selective flexing of the locking member is achieved by forming the one face of the locking member 63 which faces the one direction with a recess 65 which has a boundary adjacent the junction. In addition the edge of the locking member 63 in the region adjacent the space is formed with a set of spaced slots 67 which extend from the one face partially across the end face of the locking member and which define a set of teeth at that edge. In addition the end face 69 of the locking member is divergent away from the other face of the aperture in the opposite direction. The function of the selective flexing of the locking member 63 and the configuration of the teeth is to permit the filamentary element to be able to be pulled through the space between the locking member and the one side of the aperture in the one direction and to prevent movement of the filamentary element through the same space in the opposite direction. The engagement of the filamentary element by the locking member when the filamentary element is moving in the opposite direction is enhanced by the part annular configuration of the space through which the filamentary material is required to pass which causes the filamentary element to furrow in its passage through the space and thus engage with the free edge of the locking member. The divergent nature of the end face 69 serves to guide and enable the movement of the filamentary element in the one direction.

The head 57 of the second embodiment comprises an outer portion 71 which has a pointed conical configuration. In addition the head 57 has a barbed configuration which is provided by a set of prongs 72 which extend rearwardly from the outer portion 71 in a divergent relationship to each other. The arms 69 are spaced angularly equi-distant around the central axis of the stem 55 and each of the arms are of a generally tapered configuration with their outer ends being more convergent than the main portion of each prong 72. Because of the nature of the plastics material of which the anchor is formed the prongs are capable of resilient flexing along their length and at their junction with the stem.

Figure 4:
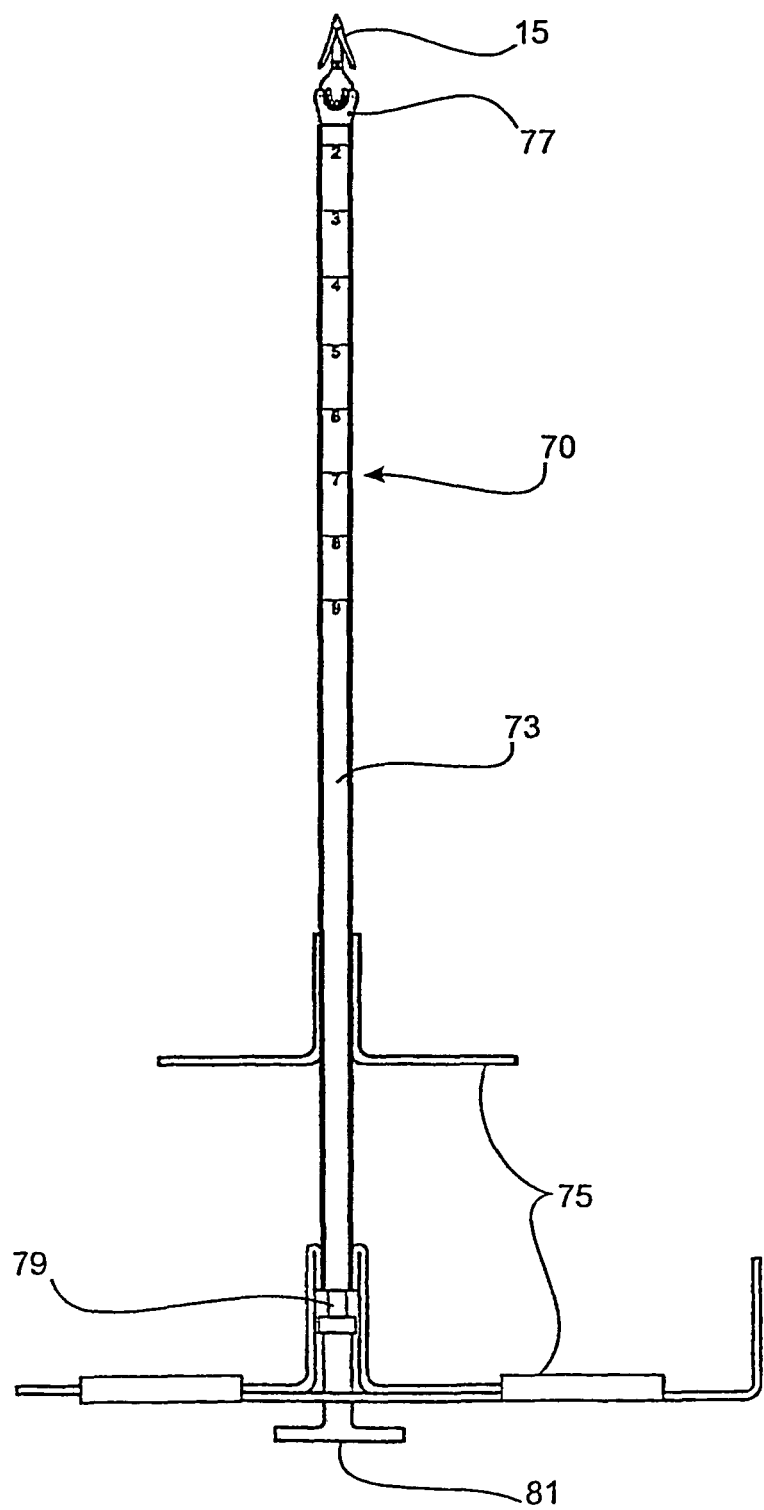
FIG. 4 is a side elevation of an insertion tool intended for use with the anchor of the second embodiment.
Figure 5:
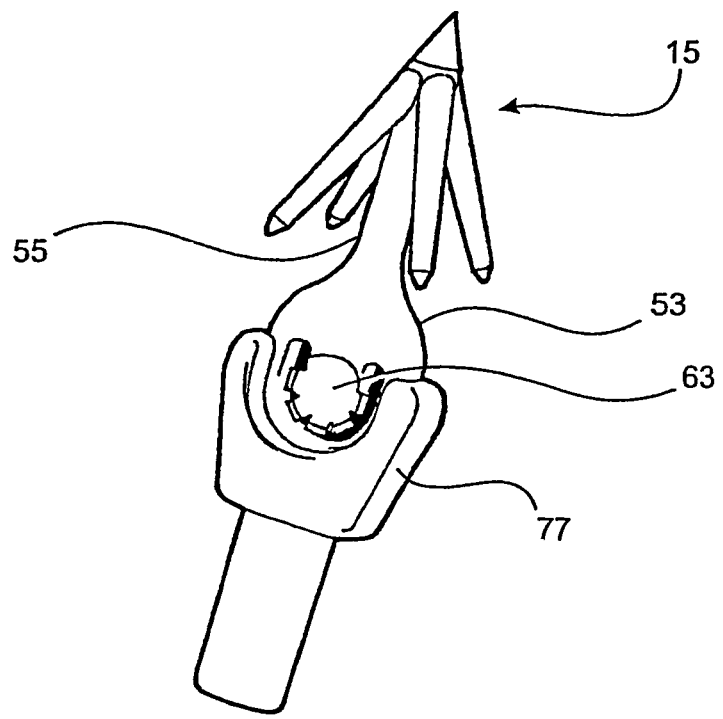
FIG. 5 is an enlarged isometric view of the end of the insertion tool supporting an anchor according to the second embodiment.
Figure 6:
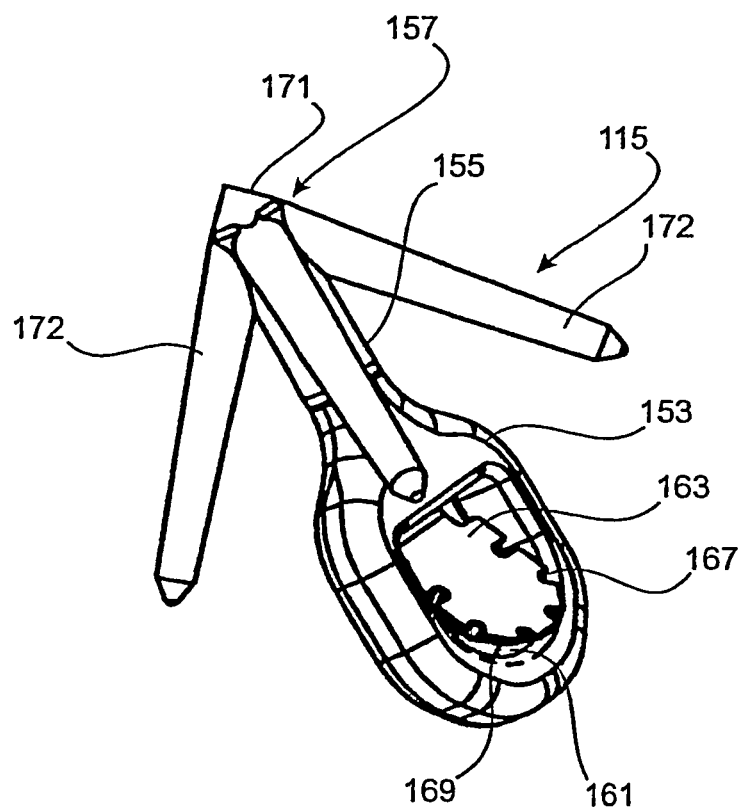
FIG. 6 is an isometric view of an anchor according to the third embodiment.
Figure 7:
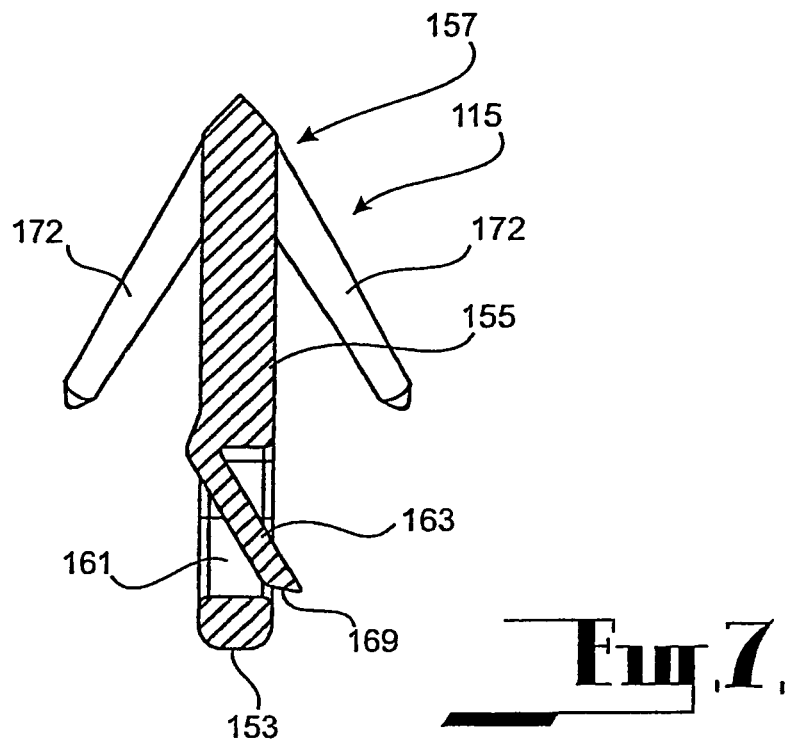
FIG. 7 is a sectional side elevation of an anchor according to the third embodiment.
Figure 8:
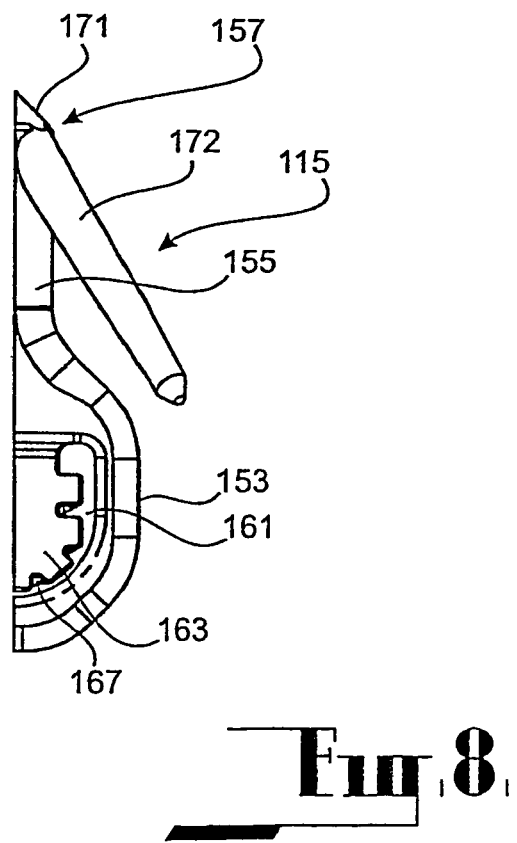
FIG. 8 is a side elevation of an anchor according to the third embodiment.

In use the anchor 15 of the second embodiment is intended to be attached to a length of the filamentary element (not shown) and the filamentary element is inserted into the body of a patient by utilisation of an insertion appliance 70 which is illustrated at FIGS. 4 and 5. The insertion appliance comprises a tubular body 73 which is provided at one end with a handle 75 and at the other end with a cradle-like support 77. The cradle-like support 77 is configured to receive the base of the anchor 15 of the second embodiment and support the anchor as shown at FIGS. 4 and 5 with the head 71 extending axially away from the end of the appliance. The internal bore of the insertion tube slidably supports a pushrod 79 which extends from the one end of the tubular body and is provided with an enlarged head 81 at its outer end The other end of the pushrod is received through a passageway through the cradle-like support 77 to terminate closely adjacent the anchor when supported in the cradle-like support 77. A suitable biasing means is provided between the tubular body 73 and the pushrod 79 to bias the pushrod to its outermost position with respect to the tubular body 73.

In use the anchor 15 is located in the cradle-like support 77 of the insertion tube and the filamentary element (not shown) is initially passed through the aperture of the anchor. The insertion tube 73 is then inserted into the body cavity through an opening in the body wall such that the free end of the insertion tube with the anchor located thereon is located against the surface of a layer of muscle tissue. With the application of an inward axial force on the enlarged head 81 of the pushrod 79, the anchor 15 is caused pass into the muscular tissue to become lodged therein. Because of the pointed configuration of the outer portion 71 of the head, the anchor 15 will move readily into engagement with the tissue, however because of the divergent nature of the arms 25, dislodgement of the anchor from the tissue is restricted. Once the anchor is firmly in position pressure is applied to the enlarged head 81 of the pushrod to displace the anchor from the cradle-like support and then the insertion appliance 70 can be removed from the body to leave the anchor and filamentary element 27 in place. A second anchor is engaged with the filamentary element at its other end and the second anchor is then fixed to another location in a similar manner using the insertion appliance. Because the filamentary element is only capable of movement through the aperture of the anchors in one direction, the length of the filamentary element supported between the anchors can be reduced, to reduce the spacing between the locations and can be tensioned.

Where the filamentary element is used to provide a sling-like support between two anchors supported in the recto-vaginal ligaments as described in relation to the first embodiment the tensioning applied to the filamentary element is such as to restore the normal tension which is expected at the at site to enable the muscular action which is available to be used to control the urethra.

The anchor 115 according to the third embodiment is shown at FIGS. 6 to 13. The anchor is formed integrally of a suitable plastics material which may be biodegradable and comprises a base 153, a stem 155 which extends from the base 153 and a head 157 which is supported in spaced relation from the base 153 by the stem 155 (at a reduced spacing compared to the second embodiment). The base is of a generally laminar configuration wherein the major faces of the base are substantially planar and parallel to the central axis of the stem 155. The base is formed with an aperture 161 which extends between the faces and which is associated with a locking member 163 which extends from the side of the aperture proximate the head 157 to terminate closely adjacent the other side of the aperture. The locking member 163 is substantially planar and is inclined with respect to the central transverse plane of the base from one face to the other face. The free edge of the locking member has a convex arcuate configuration to cooperate with the other side of the aperture to define a part annular space. The spacing between the other side of the aperture and the free edge of locking member approximately corresponds with the thickness of the filamentary element with which the anchor is to be used when the filamentary element is tensioned.

Figure 9:
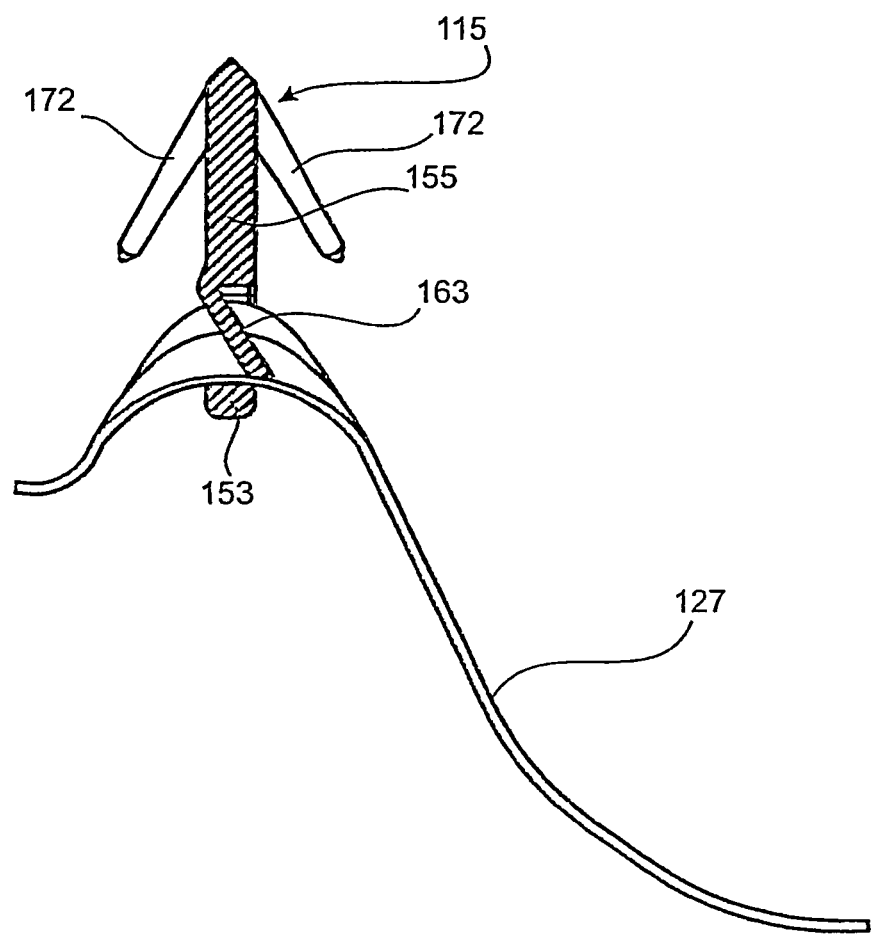
FIG. 9 is a sectional elevation of an anchor according to the third embodiment illustrating engagement between the anchor and a filamentary element.
Figure 10:
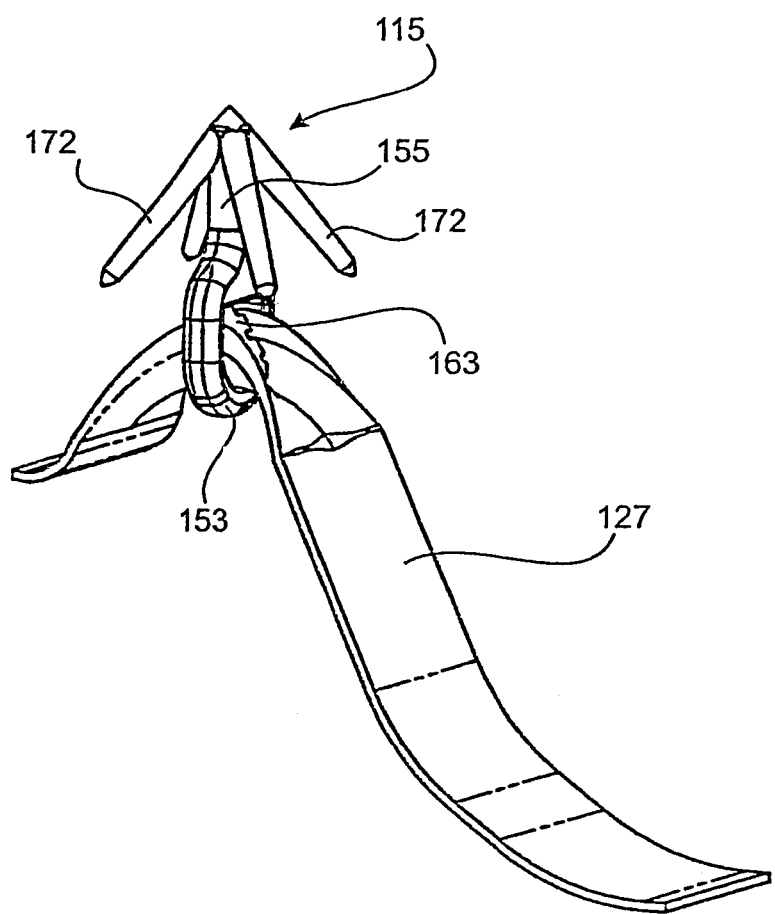
FIG. 10 is an isometric view of an anchor according to the third embodiment engaged with a filamentary element.

The locking member is of a reduced thickness compared to the thickness of the base and as a result the locking member can flex within the aperture. In addition the edge of the locking member 163 in the region adjacent the space is formed with a set of angularly spaced slots 167 which extend from the one face partially across the end face 169 of the locking member to define a set of teeth at that edge. In addition the end face 169 of the locking member is divergent away from the other face of the aperture in the opposite direction. The flexing of the locking member 163, the configuration of the teeth 167 and the configuration of the end face 169 permit the filamentary element 127 to be able to be pulled through the space between the locking member and the one side of the aperture in the one direction with substantially little interference. The divergent nature of the end face 169 serves to guide and enable the movement of the filamentary element in the one direction. In addition when the filamentary element 127 is moving in the one direction it is anticipated that it will be in a state of tension and as a result it is expected that the locking member will not interfere with the filamentary element 127 when it is moving in the one direction since the dimensions of the space will correspond with the cross section of the tensioned filamentary element 127 passing through it. However the flexing of the locking member 163, the configuration of the teeth 167 and the configuration of the end face 169 also serve to, prevent movement of the filamentary element 127 through the same space in the opposite direction. The engagement of the filamentary element 127 by the locking member when the filamentary element 127 is moving in the opposite direction is enhanced by the part annular configuration of the space through which the filamentary element 127 is required to pass which causes the filamentary element 127 to furrow in its passage through the space and thus engage with the free edge of the locking member as shown at FIGS. 9 and 10. When the filamentary element 127 is caused to move in the opposite direction the portion of the element approaching the aperture will generally not be in tension and this condition of the element together with the configuration of the space, serves to further enhance the interference that the locking member creates for movement of the filamentary element. In addition in the light of the inclined orientation of the locking member across the aperture, on movement of the filamentary element through the space in the opposite direction the interference therebetween will cause the free end of the locking member to move resiliently towards the opposite edge of the aperture and clampingly engage the filamentary element therebetween. Therefore the relationship between the locking member and the aperture serves to positively prevent the filamentary element 127 from movement in the opposite direction through the space.

The head 157 of the third embodiment comprises an outer portion 171 which has a pointed conical configuration. In addition the head 157 has a barbed configuration which is provided by a set of prongs 172 which extend rearwardly from the outer portion 171 in a divergent relationship to each other. The arms 169 are spaced angularly equidistant around the central axis of the stem 155 and each of the arms are of a generally tapered configuration with their outer ends being more convergent than the main portion of each prong 172. Because of the nature of the plastics material of which the anchor is formed the prongs are capable of resilient flexing along their length and at their junction with the stem.

Figure 12:
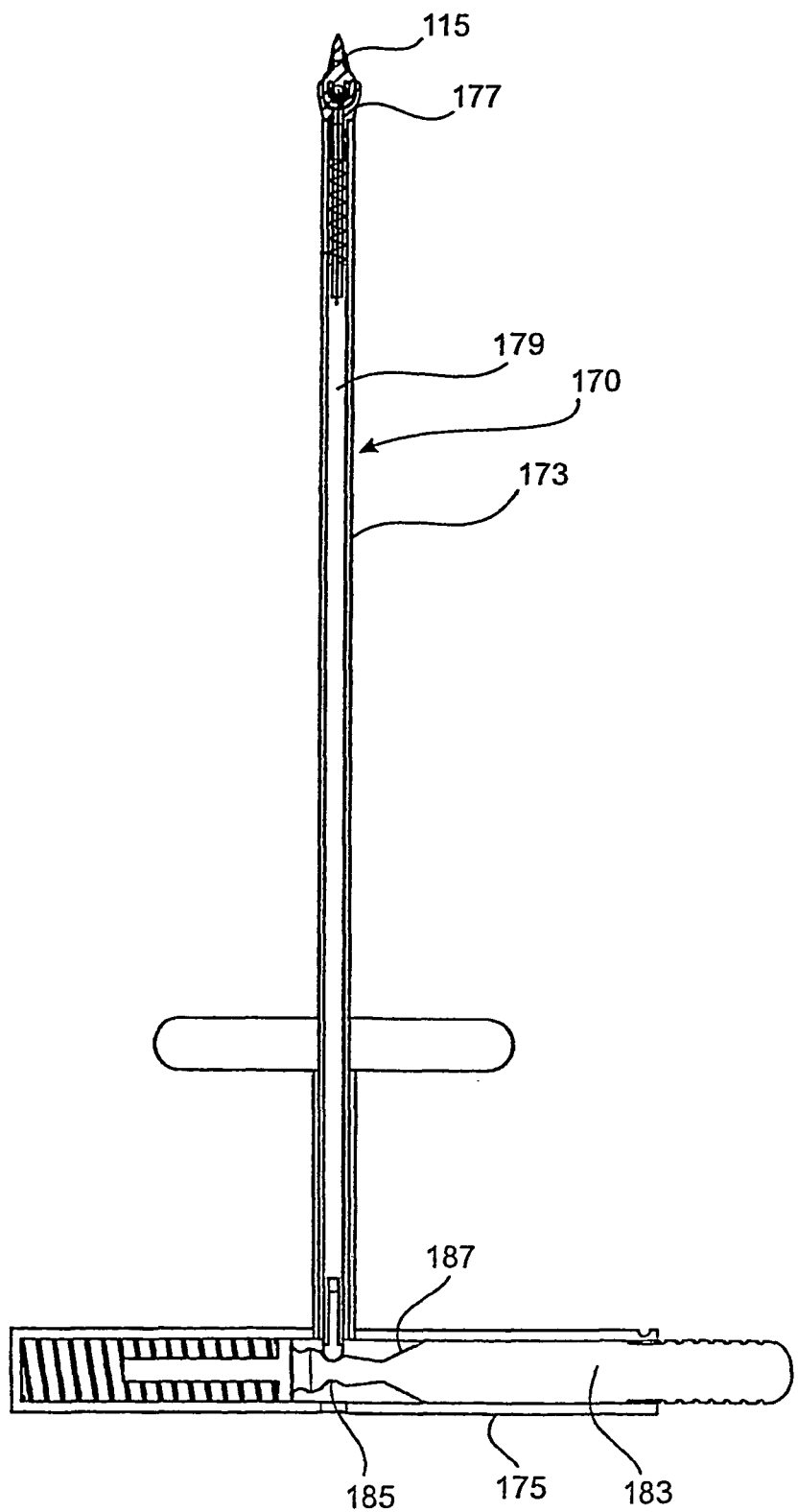
FIG. 12 is a sectional side elevation of an insertion appliance according to the third embodiment.

In use the anchor 115 of the third embodiment is intended to be attached to a length of the filamentary element as shown at FIGS. 9 and 10 and the filamentary element is inserted into the body of a patient by utilisation of an insertion appliance 170 which is illustrated at FIG. 12. The insertion appliance comprises a tubular body 173 which is provided at one end with a handle 175 and at the other end is adapted to receive a cradle-like support 177. The cradle-like support 177 is configured to receive the base of the anchor 115 of the third embodiment and support the anchor as shown at FIGS. 6 to 10 with the head 171 extending axially away from the end of the appliance. The cradle-like support is described in greater detail below. The internal bore of the insertion tube slidably supports a pushrod 179 which extends from the one end of the tubular body into the interior of the handle 175. The other end of the pushrod is received through a passageway through the cradle-like support 177 to terminate closely adjacent the anchor when supported in the cradle-like support 177. A suitable biasing means is provided between the tubular body 173 and the pushrod 179 to bias the pushrod towards the handle. The handle slidably receives a rod-shaped plunger 183 and the outer end of the pushrod 179 bears on the plunger 18. The portion of the surface of the plunger which receives the pushrod is profiled with a notched portion 185 which receives the outer end of the pushrod when in its retracted position and with an increased diameter portion 187 which will receive the outer end of the pushrod when the plunger is pushed axially inwardly into the handle to cause the pushrod to move to its extended position. When the pushrod is at its extended position it will bear upon anchor 115 supported on the cradle-like support 177 to force the anchor out of engagement with the cradle-like support 177.

Figure 11:
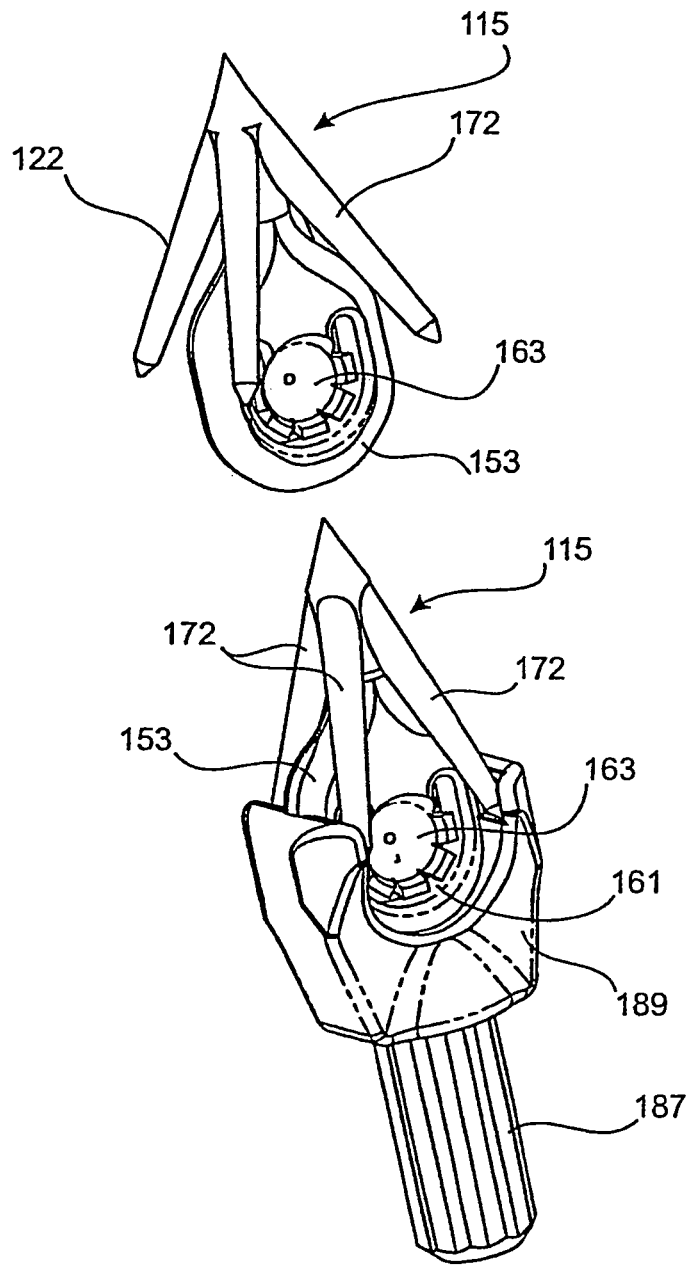
FIG. 11 is an isometric view of an anchor according to the third embodiment in engagement with a cradle like support and also illustrating the anchor out of engagement with the cradle like support.

As shown at FIG. 11 the cradle-like support comprises a central spigot 187 which is intended to be received in the end of the tubular body 173 and is configured to be frictionally engaged in the end. The outer end of the spigot supports cradle 189 which is shaped to support the base 153 of an anchor at the sides. The cradle is recessed to provide free access to the aperture 161. In addition the sides of the recess are configured at their outer ends to receive and support the free ends of the prongs 172 when compressed radially relative to each other as shown at FIG. 11. The cradle-like support is formed with a central passage which receives the pushrod 179 of the insertion appliance whereby when the pushrod is at its extended position it bears upon the base of the anchor to force it out of engagement with the cradle 189. When the anchor is free of the cradle-like support the free ends of the prongs are able to expand radially.

Figure 13:
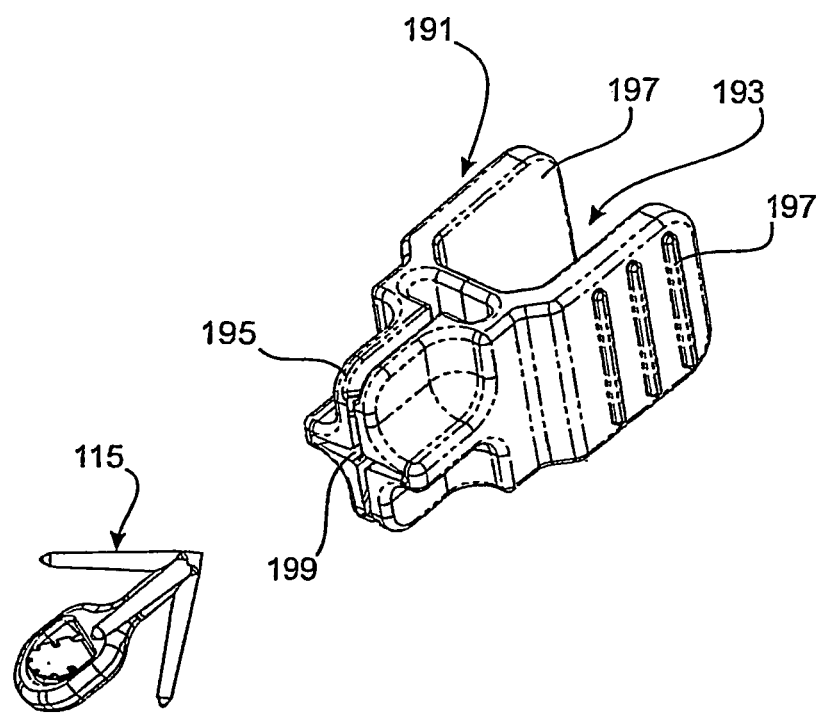
FIG. 13 is an isometric view of anchor and a holder according to the third embodiment.

To locate the anchor in position on the cradle-like support, a holder 191 of the form shown at FIG. 13 is used. The holder comprises body having a grip 193 at one end and an anchor support 195 at the other end. The grip 193 comprises a pair of opposed tabs 197 which are dimensioned and spaced from each other to be able to be engaged between a finger and thumb of the operator. The anchor support comprises a cross-like recess 199 which is configured to receive the head of the anchor, including the prongs and in so doing to radially compress the free ends of the prongs in order that they can be received in the cradle 189 of the cradle-like support.

In use the head of an anchor 115 is located in the recess of the holder and is then transferred to the cradle-like support 177 to be supported therein. This location and transfer of the anchor can be effected using the holder and without manually handling the anchor. The anchor preloaded with the filamentary element is supported in the cradle-like support. The insertion tube 173 is then inserted into the body cavity of the patient through an opening in the body wall such that the free end of the insertion tube with the anchor located thereon is located against the surface of a layer of muscle tissue. On application of additional force the head of the anchor as well as a portion of the cradle-like support is introduced into the muscle tissue. With the depression of the plunger of the insertion appliance, the pushrod 179 forces the anchor out of engagement with the cradle-like support to be received in the muscle tissue and to become lodged therein. The radial expansion of the free ends of the prongs when free of the cradle further serve to ensure retention of the anchor in the tissue. Because of the pointed configuration of the outer portion 171 of the head, the anchor 115 will move readily into engagement with the tissue, however because of the divergent nature of the prongs 125, dislodgement of the anchor from the tissue is restricted. The retention of the free ends of the prongs in the cradle enables the operator some degree of freedom in locating the anchor and the prongs are only released when the operator is satisfied with the location of the anchor. Once the anchor is firmly in position the insertion appliance 171 can be removed from the body to leave the anchor and filamentary element 127 in place. A second anchor at the other end of the filamentary element is then fixed to another location in a similar manner using the insertion appliance. Because the filamentary element is only capable of movement through the aperture of the anchors in one direction, the length of the filamentary element supported between the anchors can be reduced, to reduce the spacing between the locations and can be tensioned.

Where the filamentary element is used to provide a sling-like support between two anchors supported in the rectovaginal ligaments as described in relation to the first embodiment the tensioning applied to the filamentary element is such as to restore the normal tension which is expected at the at site enable the muscular action which is available to be used to control the urethra.

Figure 14:
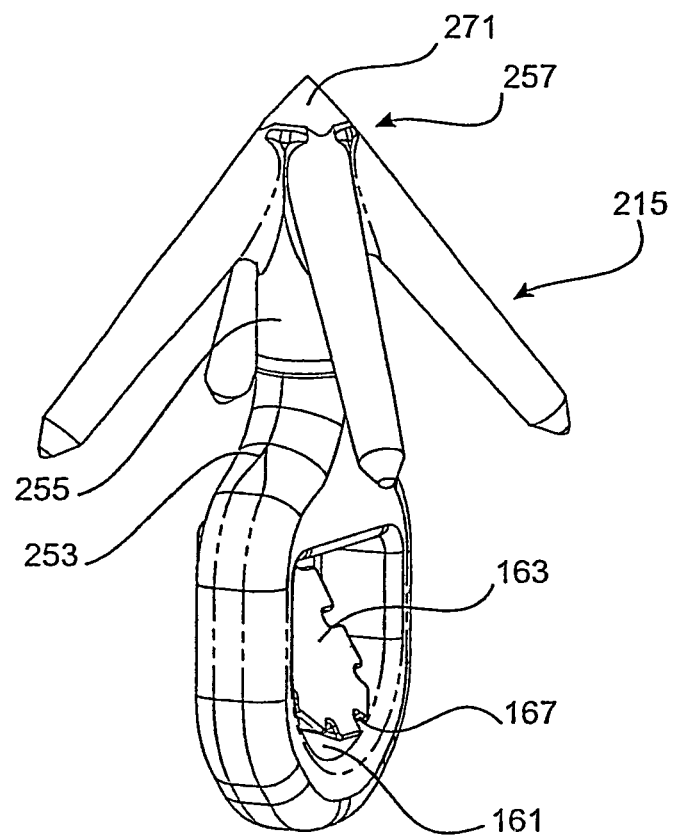
FIG. 14 is an isometric view of anchor according to the fourth embodiment.
Figure 15:
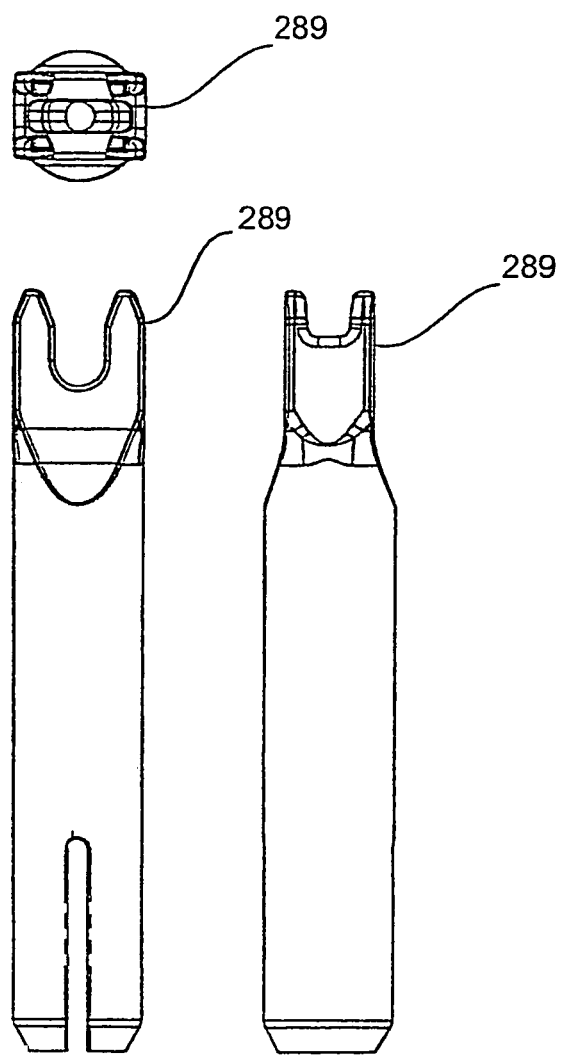
FIG. 15 is an end elevation and two side elevation of a cradle like support according to the fourth embodiment.
Figure 16:
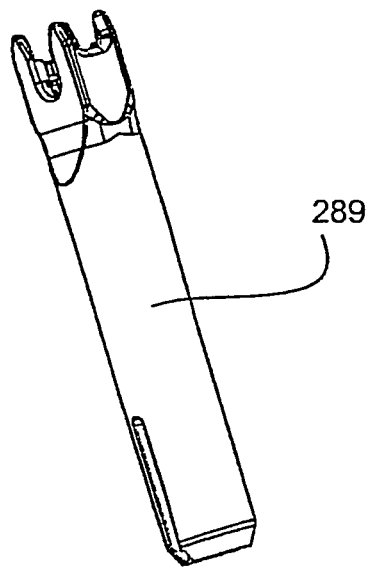
FIG. 16 are isometric views of the cradle like support according to the fourth embodiment.
Figure 16:
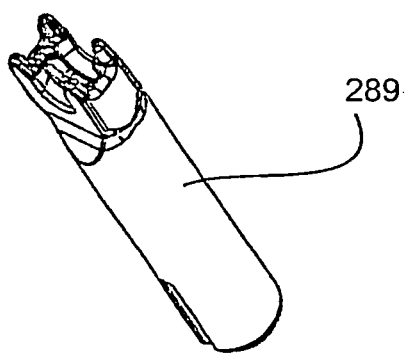
Figure 17:
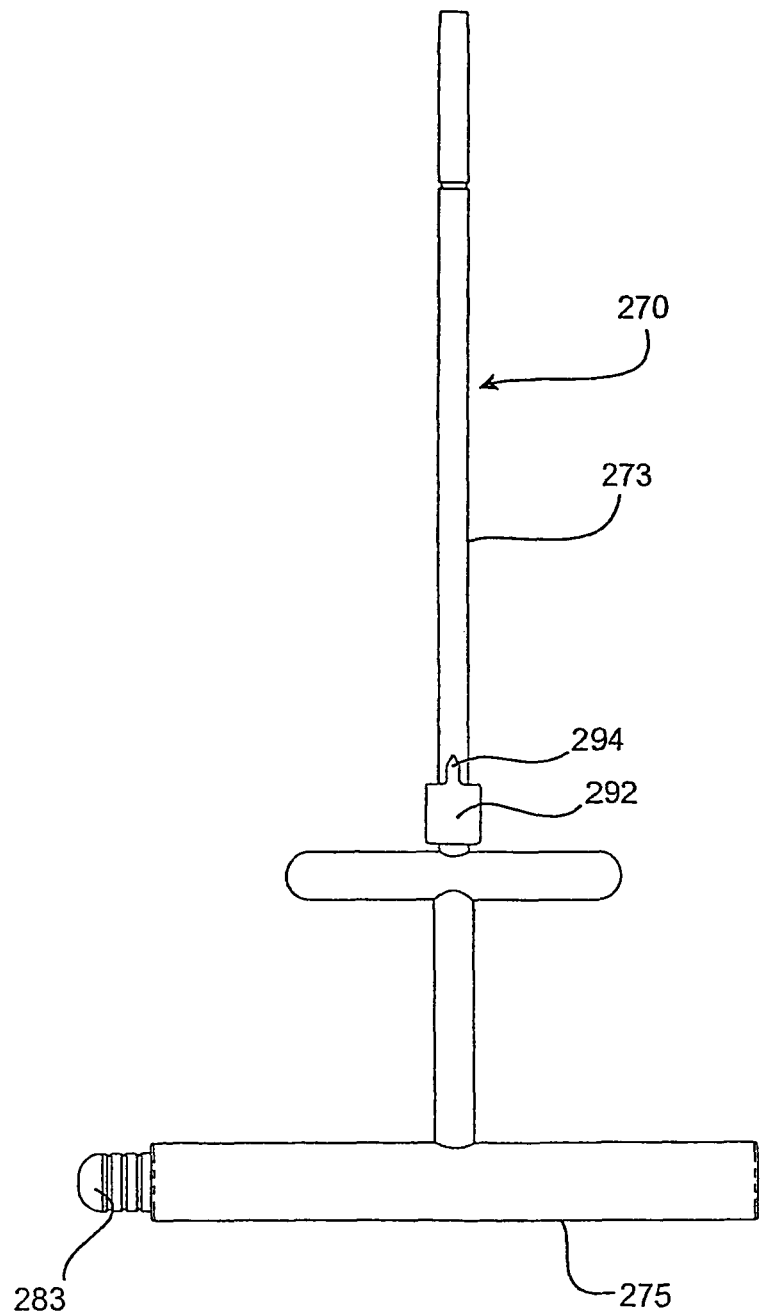
FIG. 17 is a side elevation of an insertion appliance according to the fourth embodiment.
Figure 18:
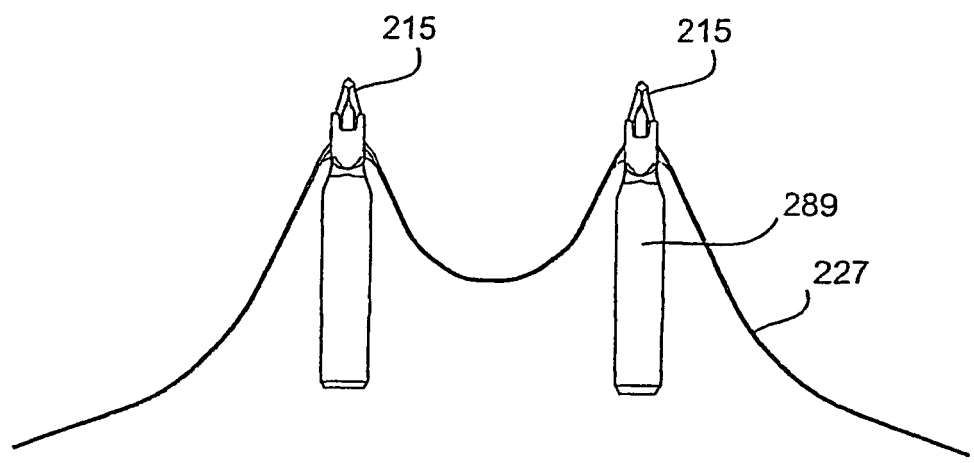
FIG. 18 is an illustration of a pair of holder like supports each accommodating an anchor which in turn is received on a filamentary element.
Figure 19:
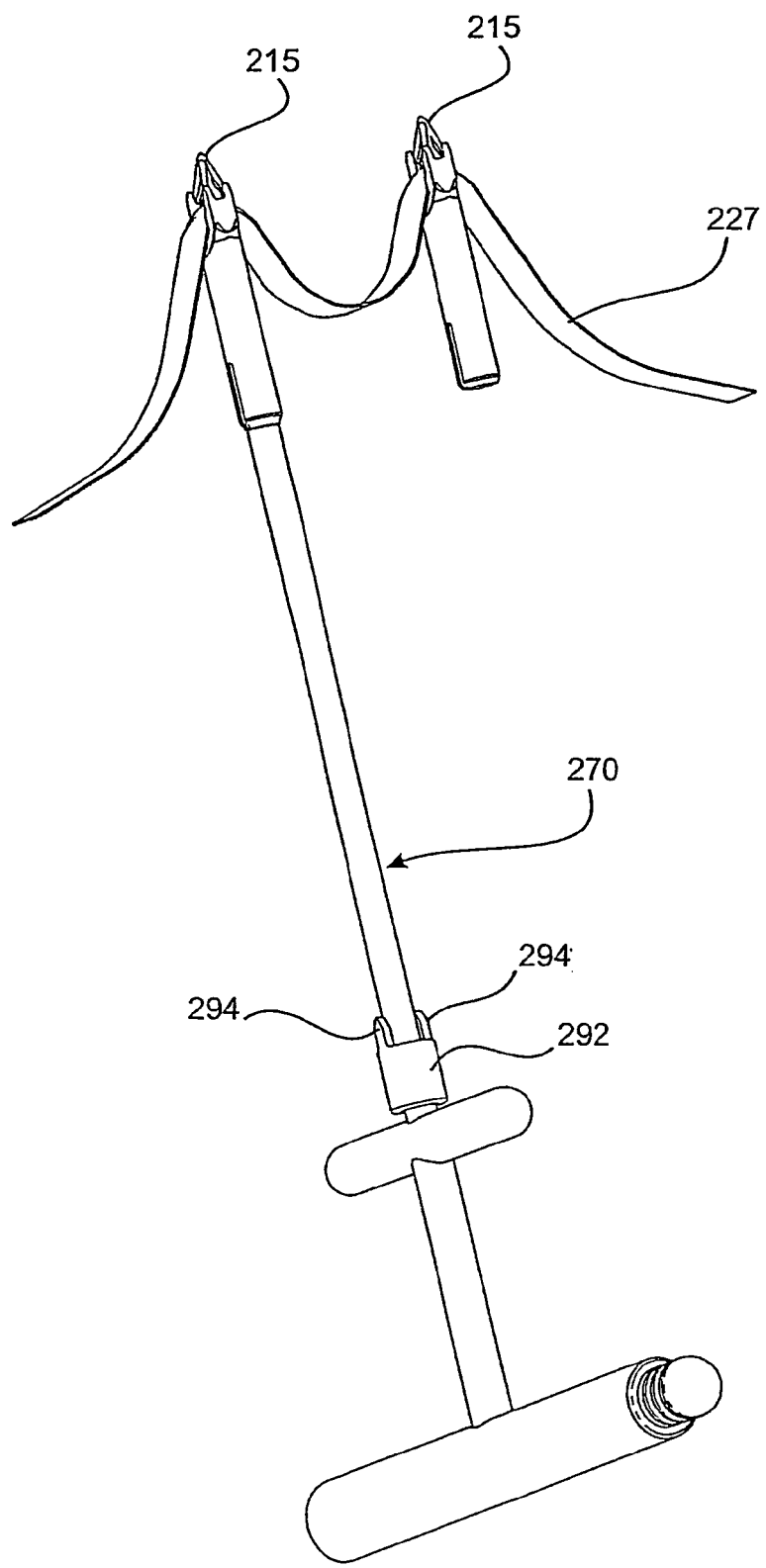
FIG. 19 is illustrative of the initial step involved in operation of the anchor for insertion.

According to a fourth embodiment as illustrated at FIGS. 14 to 21 an anchor 215 of the form as shown at FIG. 14 and which generally corresponds with an anchor according to the third embodiment is applied to a cradle-like support 277. As illustrated in FIGS. 15 and 16 the cradle-like support 277 is formed as a tubular element which is receivable over the outer end of insertion tool 270 and is formed at one end with a cradle like portion which will support and engage the anchor 215 in a similar manner to that described in relation to the third embodiment and as shown in the accompanying drawings. The configuration of the insertion appliance 270 is of the same form as that of the third embodiment. The tubular portion of the cradle-like support is formed towards its other end to be of a bifurcated configuration to allow for resilient flexing between the bifurcated portions of the tubular portion so defined when other end of the cradle-like support is applied over the outer end of the insertion appliance in order that they clampingly engage the outer surface of the tubular portion at 273 of the insertion appliance 270. If desired suitable detents may be provided in the wall of the tubular portion 273 to retain the cradle-like support in position on the end of the insertion appliance.

In addition the insertion appliance 270 is provided with a collar 292 which is slidable on the tubular portion of the insertion appliance 270. The collar 292 is provided with a pair of diametrically opposed prongs 294 which will engage in the slots between the bifurcations of the cradle-like support and with appropriate axial movement of the collar on the tubular member will cause separation between the bifurcations to facilitate removal of the cradle-like support from engagement with the insertion appliance.

Figure 20:
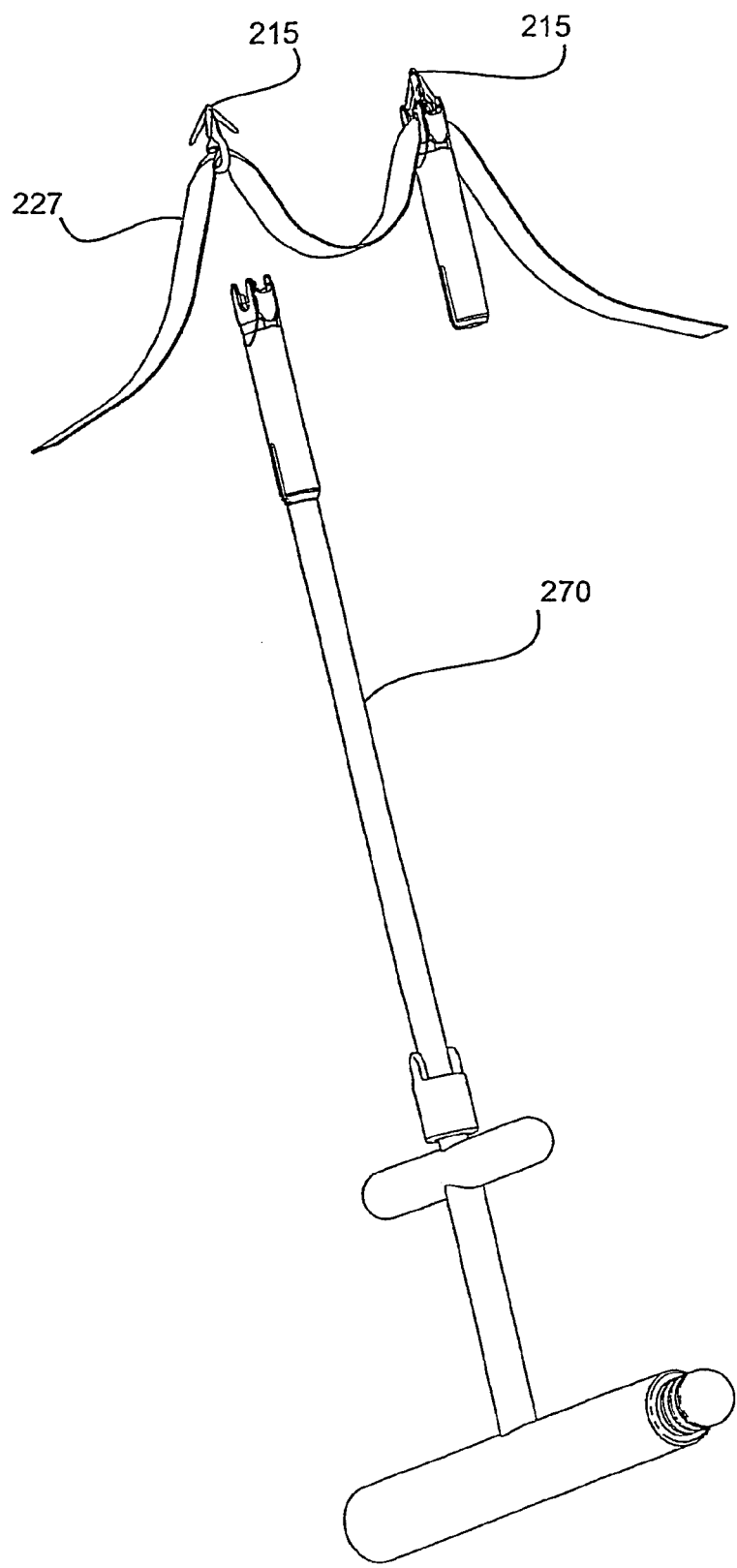
FIG. 20 is an illustrative view of the insertion appliance subsequent to release of the first anchor.
Figure 21:
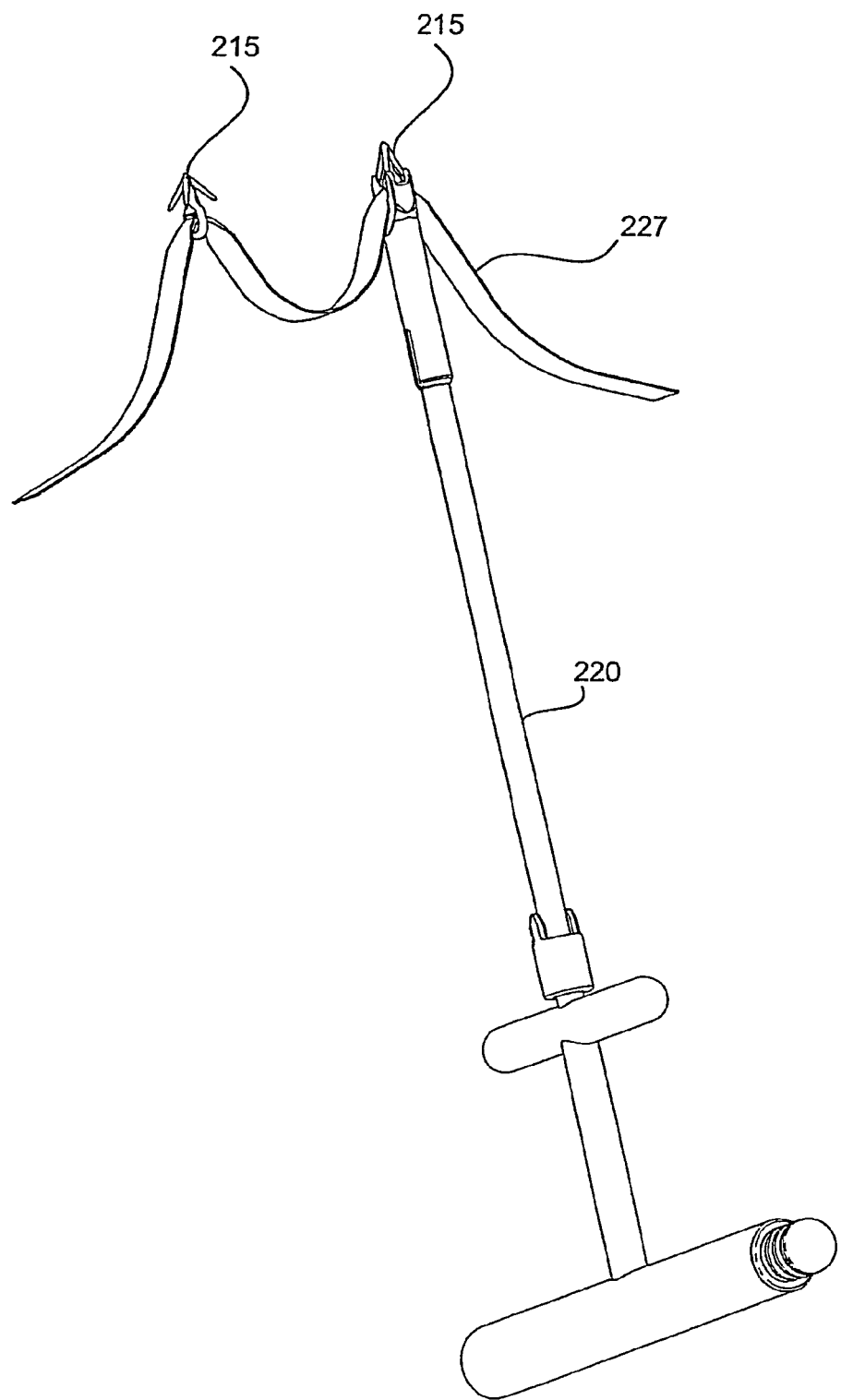
FIG. 21 is a schematic view of an insertion applicant applied to the second anchor.

In use the cradle-like support 277 and the anchor 215 is provided as a single item and it is intended that a pair of composite items be provided on a length of filamentary element 227 as a pre-packaged composite item whereby the anchors 215 are sequentially installed using an insertion tool in a manner as illustrated at FIGS. 20-21.

In an alternative application of the anchors according to the second, third and fourth embodiments they are used to directly shorten a stretched ligament or fascial tissue by inserting a pair of anchors into a ligament at spaced intervals along the ligament and shortening the ligament or fascial tissue by tensioning the filamentary element between the anchors.

Throughout the specification, unless the context requires otherwise, the word "comprise" or variations such as "comprises" or "comprising", will be understood to imply the inclusion of a stated integer or group of integers but not the exclusion of any other integer or group of integers.

It should be appreciated that the scope of the invention need not be limited to the particular scope of the embodiment described above and in particular is not restricted to the particular example of application of the embodiment described above.

The invention claimed is:

1. A tissue anchor formed of a material which is compatible for location in human and/or animal muscle and/or ligament tissue and/or tissue, the anchor comprising:
a base and a head, the head including a plurality of tapered prongs that form a barbed configuration to facilitate insertion of the head into the tissue and retention of the anchor following insertion of the head in the tissue, the base including an aperture having a longitudinal length between a first side and a second side and a locking element, said locking element extending from said first side of the aperture to terminate at a free end closely adjacent to said second side of the aperture to define a space between the free end of the locking element and the second side of the aperture for receiving a filamentary element, the locking element arranged to flex in a first direction out of the plane of the aperture and be resistant to movement in a second direction out of the plane of the aperture, the locking element having a first face facing the first direction and a second face facing the second direction, the locking element further including a set of teeth arranged to engage with the filamentary element when it is pulled in the second direction through the space, the set of teeth are defined by spaced slots extending from the first face to the second face, the set of teeth and flexure of the locking element thereby permitting the filamentary element to be pulled in the first direction through the space whilst preventing the filamentary element from being pulled in the second direction through the space, wherein the free end of the locking element has a convex arcuate configuration and the space is annular.

2. A tissue anchor as claimed in claim 1 wherein the space has a configuration substantially corresponding to the cross section of the filamentary element.

3. A tissue anchor as claimed in claim 2 wherein the space has a configuration corresponding to the cross sectional configuration of the filamentary element when under longitudinal tension.

4. A tissue anchor as claimed in claim 1 wherein the space is located substantially centrally across the central lonaitudinal axis of the anchor.

5. A tissue anchor as claimed in claim 1 wherein the locking member is inclined with respect to the base.

6. A tissue anchor as claimed in claim 1 wherein the prongs are located in substantially equidistant spacing around the central axis of the head, and the prongs diverge away from the end of the head in the direction of the base.

7. A tissue anchor as claimed in claim 1 wherein the outer end of the prongs are pointed.

8. A tissue anchor as claimed in claim 1 wherein the prongs are resiliently flexible along their length.

9. A tissue anchor as claimed in claim 1 wherein the locking element forms a flexible junction with the aperture such that movement of the locking element in said one direction increases the space between the second edge of the aperture and the locking element, and movement of the locking element in said opposite direction acts to decrease the space between the second edge of the aperture and the locking element.

10. A tissue anchor as claimed in claim 1, wherein the head is formed with a pointed tip.

11. A tissue anchor as claimed in claim 1, wherein said prongs extend radially backward from said head.

12. A tissue anchor according to claim 1 wherein the free end of the locking element has an end face that diverges away from the second side of the aperture towards the second direction.

13. A tissue anchor according to claim 1 wherein the configuration of the space between the free end of the locking element and the second side of the aperture causes the filamentary element to furrow in its passage through the space so as to engage with the free end of the locking element when it is pulled in the second direction through the space.

14. A tissue anchor according to claim 1 wherein the filamentary element is a woven or knitted tape.

15. A tissue anchor according to claim 1 wherein the spaced slots are formed in an edge of the locking element.

16. A tissue anchor according to claim 1 including four tapered prongs.

17. A tissue anchor according to claim 1 wherein the aperture is located in the base distal of the tapered prongs.

18. A tissue anchor according to claim 1 wherein said base is attached to said head.

19. A tissue anchor according to claim 1 wherein said locking member includes a front surface disposed at an acute angle with respect to said aperture and said free face is defined by an edge surface disposed at an acute angle with respect to said front surface.

20. And be resistant to movement in a second direction out of plane of the aperture, the locking element having a first face facing the first direction and a second face facing the second direction, the locking element including a set of teeth arranged to engage with the filamentary element when it is pulled in the second direction through the space, the set of teeth are defined by spaced slots extending from the first face to the second face, the set of teeth and flexure of the locking element permitting the filamentary element to be pulled in the first direction through the space whilst preventing the filamentary element from being pulled in the second direction through the space, wherein the free end of the locking element has a convex arcuate configuration and the space is annular.

21. The tissue anchor of claim 20 wherein said locking element is integral with said base.

22. The tissue anchor of claim 20 wherein said locking element is attached to and integral with said first side.

* * * * *

UNITED STATES PATENT AND TRADEMARK OFFICE
CERTIFICATE OF CORRECTION

PATENT NO. : 8,753,372 B2
APPLICATION NO. : 10/524701
DATED : June 17, 2014
INVENTOR(S) : Petros It is certified that error appears in the above-identified patent and that said Letters Patent is hereby corrected as shown below:

In the claims

Column 12, line 61 - Column 13, line 6 before the words "And be resistant to move..", insert -- A tissue anchor formed of a material which is compatible for location in human and/or animal muscle and/or ligament tissue and/or tissue, the anchor comprising:
a head including a plurality of prongs arranged and configured to facilitate insertion of the head into the tissue and retention of the anchor following insertion of the head in the tissue; and
a base including:
an aperture having a longitudinal length between a first side and a second side and
a locking element, said locking element extending from said first side of the aperture to terminate at a free end closely adjacent to said second side of the aperture to define a space between the free end of the locking element and the second side of the aperture for receiving a filamentary element, the locking element arranged to flex in a first direction out of the plane of the aperture --

Signed and Sealed this
Nineteenth Day of January, 2016

Michelle K. Lee
*Director of the United States Patent and Trademark Office*